United States Patent
Gonzalez et al.

(10) Patent No.: US 8,247,341 B2
(45) Date of Patent: Aug. 21, 2012

(54) PROCATALYST COMPOSITION WITH SILYL GLUTARATE AND METHOD

(75) Inventors: Kelly A. Gonzalez, Katy, TX (US); Tao Tao, Houston, TX (US); Tak W. Leung, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 219 days.

(21) Appl. No.: 12/760,070

(22) Filed: Apr. 14, 2010

(65) Prior Publication Data

US 2010/0267911 A1    Oct. 21, 2010

Related U.S. Application Data

(60) Provisional application No. 61/170,332, filed on Apr. 17, 2009.

(51) Int. Cl.
*C08F 4/02* (2006.01)
*C08F 4/06* (2006.01)
*C08F 4/44* (2006.01)
*C08F 2/00* (2006.01)
*B01J 21/00* (2006.01)

(52) U.S. Cl. ........ 502/116; 502/127; 502/158; 502/232; 526/126; 526/128; 526/213

(58) Field of Classification Search ............... 502/116, 502/158, 232; 526/126, 128, 213
See application file for complete search history.

(56) References Cited

U.S. PATENT DOCUMENTS

| | | | |
|---|---|---|---|
| 4,442,276 A | 4/1984 | Kashiwa et al. | |
| 4,460,701 A | 7/1984 | Terano et al. | |
| 4,540,679 A | 9/1985 | Arzoumanidis et al. | |
| 4,547,476 A | 10/1985 | Terano et al. | |
| 4,816,433 A | 3/1989 | Terano et al. | |
| 4,829,037 A | 5/1989 | Terano et al. | |
| 4,927,797 A | 5/1990 | Ewen | |
| 4,990,479 A | 2/1991 | Ishimaru et al. | |
| 5,028,671 A | 7/1991 | Kioka et al. | |
| 5,034,361 A | 7/1991 | Job et al. | |
| 5,066,737 A | 11/1991 | Job | |
| 5,066,738 A | 11/1991 | Ewen | |
| 5,077,357 A | 12/1991 | Job | |
| 5,082,907 A | 1/1992 | Job | |
| 5,106,806 A | 4/1992 | Job | |
| 5,146,028 A | 9/1992 | Job | |
| 5,151,399 A | 9/1992 | Job | |
| 5,153,158 A | 10/1992 | Kioka et al. | |
| 5,229,342 A | 7/1993 | Job | |
| 5,247,031 A | 9/1993 | Kioka et al. | |
| 5,247,032 A | 9/1993 | Kioka et al. | |
| 6,541,582 B1 * | 4/2003 | Morini et al. | 526/124.3 |
| 6,825,146 B2 | 11/2004 | Kilty et al. | |
| 7,388,061 B2 | 6/2008 | Gao et al. | |

FOREIGN PATENT DOCUMENTS

| | | |
|---|---|---|
| DE | 238976 A1 | 9/1986 |
| EP | 1746110 A1 | 1/2007 |
| WO | 00/55215 A1 | 9/2000 |

OTHER PUBLICATIONS

Djerourou et al., Journal of Organometallic Chemistry 485(1995) 63-68.
Barnier et al., Journal of Organometallic Chemistry 514(1996) 67-71.

* cited by examiner

*Primary Examiner* — David W Wu
*Assistant Examiner* — Elizabeth Eng
(74) *Attorney, Agent, or Firm* — Whyte Hirschboeck Dudek SC

(57) ABSTRACT

Disclosed are procatalyst compositions having an internal electron donor which includes a silyl glutarate and optionally an electron donor component. Ziegler-Natta catalyst compositions containing the present procatalyst compositions exhibit strong activity and produce propylene-based olefins with high isotacticity.

20 Claims, No Drawings

PROCATALYST COMPOSITION WITH SILYL GLUTARATE AND METHOD

CROSS REFERENCE TO RELATED APPLICATION

This claims the benefit of U.S. Provisional Application No. 61/170,332 filed Apr. 17, 2009.

BACKGROUND

The present disclosure relates to procatalyst compositions containing a silyl glutarate and the incorporation of the same in catalyst compositions and the resultant olefin-based polymers produced therefrom.

Worldwide demand for olefin-based polymers continues to grow as applications for these polymers become more diverse and more sophisticated. Known are Ziegler-Natta catalyst compositions for the production of olefin-based polymers. Ziegler-Natta catalyst compositions typically include a procatalyst composed of a transition metal halide (i.e., titanium, chromium, vanadium) supported on a magnesium compound, the procatalyst complexed with a cocatalyst such as an organoaluminum compound. Given the perennial emergence of new applications for olefin-based polymers, the art recognizes the need for olefin-based polymers with improved and varied properties. Desirable would be Ziegler-Natta catalyst compositions for the production olefin-based polymers that exhibit strong catalyst activity during polymerization and produce propylene-based polymers with high stereoregularity. Further desired is a catalyst composition that can be used to manipulate the molecular weight distribution of the resultant polymer.

SUMMARY

The present disclosure is directed to procatalyst compositions containing a silyl glutarate and the application of the same in procatalyst compositions, catalyst compositions, and polymerization processes. The silyl glutarate-containing catalyst compositions of the present disclosure demonstrate strong activity during polymerization. In addition, the present silyl glutarate-containing catalyst compositions produce propylene-based olefins with high stereoregularity.

In an embodiment, a composition is provided. The composition includes a silyl glutarate having the structure (I).

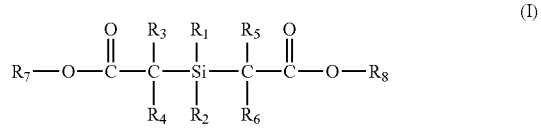

$R_1$-$R_8$ are the same or different. Each of $R_1$ and $R_2$ is selected from hydrogen and a saturated hydrocarbyl group having 1-6 carbon atoms. Each of $R_3$-$R_6$ is selected from hydrogen and a hydrocarbyl group having 1-10 carbon atoms. Each of $R_7$-$R_8$ is selected from a hydrocarbyl group having 1-2 carbon atoms. $R_1$, $R_2$, $R_7$, and $R_8$ are simultaneously not a methyl group.

In an embodiment, a process for producing a procatalyst composition is provided. The process includes reacting a silyl glutarate, a procatalyst precursor and a halogenating agent. The reaction occurs in a reaction mixture. The reaction forms a procatalyst composition comprising a magnesium moiety, a titanium moiety, and an internal electron donor comprising the silyl glutarate.

In an embodiment, a procatalyst composition is provided. The procatalyst composition includes a combination of a magnesium moiety, a titanium moiety and an internal electron donor. The internal electron donor includes a silyl glutarate. The magnesium moiety and/or the titanium moiety may be a respective halide.

In an embodiment, the silyl glutarate has the structure (I) as disclosed above. $R_1$-$R_8$ are the same or different. Each of $R_1$-$R_6$ is selected from hydrogen, a substituted hydrocarbyl group having 1 to 20 carbon atoms, an unsubstituted hydrocarbyl group having 1 to 20 carbon atoms, and combinations thereof. Each of $R_7$-$R_8$ is selected from a substituted hydrocarbyl group having 1 to 20 carbon atoms and an unsubstituted hydrocarbyl group having 1 to 20 carbon atoms.

In an embodiment, $R_1$ and $R_2$ are the same or different. Each of $R_1$ and $R_2$ is selected from hydrogen, a $C_1$-$C_6$ alkyl group, and combinations thereof.

In an embodiment, $R_7$ and $R_8$ are the same or different. Each of $R_7$ and $R_8$ is selected from a $C_1$-$C_6$ alkyl group.

In an embodiment, the procatalyst composition contains from about 0.01 wt % to about 1.5 wt % ethoxide.

In an embodiment, the procatalyst composition contains from about 0.1 wt % to about 18 wt % silyl glutarate.

In an embodiment, another procatalyst composition is provided. The procatalyst composition includes a combination of a magnesium moiety, a titanium moiety and a mixed internal electron donor. The mixed internal electron donor includes a silyl glutarate and an electron donor component. The electron donor component may be a phthalate, ethyl benzoate, a diether and combinations thereof.

In an embodiment, a catalyst composition is provided. The catalyst composition includes a procatalyst composition comprising a silyl glutarate. The catalyst composition also includes a cocatalyst. The catalyst composition may optionally include an external electron donor, an activity limiting agent, and combinations thereof.

In an embodiment, the catalyst composition includes an internal electron donor that is a silyl glutarate.

In an embodiment, the catalyst composition includes a mixed internal electron donor. The mixed internal electron donor includes a silyl glutarate and an electron donor component as described above.

In an embodiment, the catalyst composition includes an external electron donor, a mixed external electron donor, and/or an activity limiting agent. The external electron donor may include an alkoxysilane.

In an embodiment, a process for producing an olefin-based polymer is provided. The process includes contacting, under polymerization conditions, an olefin with a catalyst composition. The catalyst composition includes a silyl glutarate. The process further includes forming an olefin-based polymer.

In an embodiment, the olefin is propylene. The process includes forming a propylene-based polymer having a polydispersity index from about 3.0 to about 8.0.

In an embodiment, the olefin is propylene. The process includes forming a propylene-based polymer having a melt flow rate from about 0.01 g/10 min to about 800 g/10 min.

An advantage of the present disclosure is the provision of an improved procatalyst composition.

An advantage of the present disclosure is the provision of an improved catalyst composition for the polymerization of olefin-based polymers.

An advantage of the present disclosure is a catalyst composition that contains a silyl glutarate, the catalyst composition exhibiting improved activity during polymerization.

An advantage of the present disclosure is a catalyst composition comprising a silyl glutarate that produces a propylene-based polymer with high stereoregularity.

An advantage of the present disclosure is a catalyst composition that contains a silyl glutarate that produces a propylene-based polymer with a narrow molecular weight distribution.

DETAILED DESCRIPTION

In an embodiment, the present disclosure is directed to compositions containing a silyl glutarate having the structure (I):

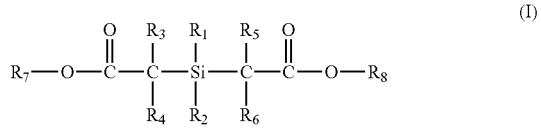

wherein $R_1$-$R_8$ are the same or different. Each of $R_1$-$R_6$ is selected from hydrogen, a substituted hydrocarbyl group having 1 to 20 carbon atoms, an unsubstituted hydrocarbyl group having 1 to 20 carbon atoms, and combinations thereof. Each of $R_7$-$R_8$ is selected from a substituted hydrocarbyl group having 1 to 20 carbon atoms, an unsubstituted hydrocarbyl group having 1 to 20 carbon atoms, and combinations thereof. As used herein, the term "hydrocarbyl" and "hydrocarbon" refer to substituents containing only hydrogen and carbon atoms, including branched or unbranched, saturated or unsaturated, cyclic, polycyclic or noncyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

As used herein, the terms "substituted hydrocarbyl" and "substituted hydrocarbon" refer to a hydrocarbyl group that is substituted with one or more nonhydrocarbyl substituent groups. A nonlimiting example of a nonhydrocarbyl substituent group is a heteroatom. As used herein, a "heteroatom" refers to an atom other than carbon or hydrogen. The heteroatom can be a non-carbon atom from Groups IV, V, VI, and VII of the Periodic Table. Nonlimiting examples of heteroatoms include: halogens (F, Cl, I, Br), N, O, P, B, S, and Si. As used herein, the term "halohydrocarbyl" refers to a hydrocarbyl that is substituted with one or more halogen atoms.

In an embodiment, a composition is provided. The composition includes a silyl glutarate having the structure (I):

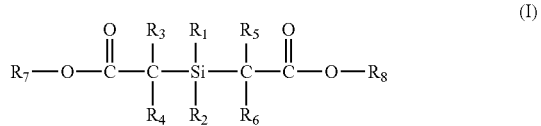

wherein $R_1$-$R_8$ are the same or different. Each of $R_1$-$R_2$ is selected from hydrogen and a saturated hydrocarbyl group having 1-6 carbon atoms. Each of $R_3$-$R_6$ is selected from hydrogen and a hydrocarbyl group having 1-10 carbon atoms. Each of $R_7$ and $R_8$ is selected from a hydrocarbyl group having 1-2 carbon atoms. $R_1$, $R_2$, $R_7$ and $R_8$ are simultaneously not a methyl group.

In an embodiment, $R_1$ and $R_2$ of structure (I) are the same or different. Each of $R_1$ and $R_2$ is selected from a saturated hydrocarbyl group having 1 to 4 carbon atoms.

In an embodiment, each of $R_3$-$R_6$ is a hydrogen atom.

In an embodiment, $R_1$ and $R_2$ of structure (I) are selected from an unsubstituted hydrocarbyl group having 3 to 4 carbon atoms. Each of $R_7$ and $R_8$ of structure (I) is a hydrocarbyl group having 2 carbon atoms.

In an embodiment, the composition includes diethyl 2,2'-(diisopropylsilanediyl)diacetate.

In an embodiment, the composition includes diethyl 2,2'-(dimethylsilanediyl)diacetate.

In an embodiment, the composition includes diethyl 2,2'-(diisobutylsilanediyl)diacetate.

In an embodiment, a process for producing a procatalyst composition is provided. The process includes reacting a silyl glutarate, a procatalyst precursor and a halogenating agent. The reaction occurs in a reaction mixture. The reaction results in the formation of a procatalyst composition. The procatalyst composition includes a magnesium moiety, a titanium moiety, and an internal electron donor. The internal electron donor includes a silyl glutarate.

In an embodiment, the silyl glutarate has the structure (I) below:

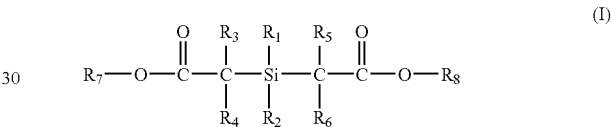

wherein $R_1$-$R_8$ are the same or different. Each of $R_1$-$R_6$ is selected from hydrogen, a substituted hydrocarbyl group having 1 to 20 carbon atoms, an unsubstituted hydrocarbyl group having 1 to 20 carbon atoms, and combinations thereof. Each of $R_7$-$R_8$ is selected from a substituted hydrocarbyl group having 1-20 carbon atoms and an unsubstituted hydrocarbyl group having 1-20 carbon atoms.

The procatalyst precursor can include (i) magnesium; (ii) a transition metal compound of an element from Periodic Table groups IV to VIII; (iii) a halide, an oxyhalide, and/or an alkoxide of (i) and/or (ii); and (iv) combinations of (i), (ii), and (iii). Nonlimiting examples of suitable procatalyst precursors include halides, oxyhalides, and alkoxides of magnesium, titanium, vanadium, chromium, molybdenum, zirconium, hafnium, and combinations thereof.

Various methods of making procatalyst precursors are known in the art. These methods are described, inter alia, in U.S. Pat. Nos. 6,825,146, 5,034,361; 5,082,907; 5,151,399; 5,229,342; 5,106,806; 5,146,028; 5,066,737; 5,077,357; 4,442,276; 4,540,679; 4,547,476; 4,460,701; 4816,433; 4,829,037; 4,927,797; 4,990,479; 5,066,738; 5,028,671; 5,153,158; 5,247,031; 5,247,032, and elsewhere. In an embodiment, the preparation of the procatalyst precursor involves halogenation of mixed magnesium and titanium alkoxides, and may involve the use of one or more compounds, referred to as "clipping agents", that aid in forming specific, low molecular weight, compositions of the desired morphology. Nonlimiting examples of suitable clipping agents include trialkylborates, especially triethylborate, phenolic compounds, especially cresol, and silanes.

In an embodiment, the procatalyst precursor is a magnesium moiety compound (MagMo), a mixed magnesium titanium compound (MagTi), or a benzoate-containing magnesium chloride compound (BenMag). In one embodiment, the procatalyst precursor is a magnesium moiety ("MagMo") precursor. The MagMo precursor contains magnesium as the sole metal component. The MagMo precursor includes a magnesium moiety. Nonlimiting examples of suitable magnesium moieties include anhydrous magnesium chloride and/or its alcohol adduct, magnesium alkoxide or aryloxide, mixed magnesium alkoxy halide, and/or carboxylated magnesium dialkoxide or aryloxide. In another embodiment, the MagMo precursor is a magnesium di($C_{1-4}$)alkoxide. In a further embodiment, the MagMo precursor is diethoxymagnesium.

In an embodiment, the procatalyst precursor is a mixed magnesium/titanium compound ("MagTi"). The "MagTi precursor" has the formula $Mg_dTi(OR^e)_fX_g$ wherein $R^e$ is an aliphatic or aromatic hydrocarbon radical having 1 to 14 carbon atoms or COR' wherein R' is an aliphatic or aromatic hydrocarbon radical having 1 to 14 carbon atoms; each $OR^e$ group is the same or different; X is independently chlorine, bromine or iodine, preferably chlorine; d is 0.5 to 56, or 2 to 4; f is 2 to 116 or 5-15; and g is 0.5 to 116, or 1 to 3. The MagTi precursor is prepared by controlled precipitation through removal of an alcohol from the reaction mixture used in its preparation. In an embodiment, a reaction medium comprises a mixture of an aromatic liquid, especially a chlorinated aromatic compound, most especially chlorobenzene, with an alkanol, especially ethanol. Suitable halogenating agents include titanium tetrabromide, titanium tetrachloride or titanium trichloride, especially titanium tetrachloride. Removal of the alkanol from the solution used in the halogenation, results in precipitation of the solid precursor, having desirable morphology and surface area. Moreover, the resulting precursors are particularly uniform in particle size.

In an embodiment, the procatalyst precursor is a benzoate-containing magnesium chloride compound ("BenMag"). As used herein, a "benzoate-containing magnesium chloride" ("BenMag") is a procatalyst (i.e., a procatalyst precursor that has been halogenated) containing a benzoate internal electron donor. The BenMag compound may also include a titanium moiety, such as a titanium halide. The benzoate internal donor is labile and can be replaced by other electron donors during procatalyst and/or catalyst synthesis. Nonlimiting examples of suitable benzoate groups include ethyl benzoate, methyl benzoate, p-methoxy ethyl benzoate, p-ethoxy methyl benzoate, p-ethoxy ethyl benzoate, and p-chloro ethyl benzoate. In one embodiment, the benzoate group is ethyl benzoate. Nonlimiting examples of suitable BenMag procatalyst precursors include catalysts of the trade names SHAC 103 and SHAC 310 available from The Dow Chemical Company, Midland, Mich.

The present procatalyst composition also includes an internal electron donor. As used herein, an "internal electron donor" is a compound added or otherwise formed during formation of the procatalyst composition that donates at least one a pair of electrons to one or more metals present in the resultant procatalyst composition. Not bounded by any particular theory, it is believed that the internal electron donor assists in regulating the formation of active sites and thus enhances stereoselectivity. In an embodiment, the internal electron donor includes a silyl glutarate of structure (I).

In an embodiment, the procatalyst precursor is converted to a solid procatalyst by way of halogenation and titanation. Halogenation and titanation include contacting the procatalyst precursor with a halogenating agent and a titanating agent in the presence of the internal electron donor. A "halogenating agent," as used herein, is a compound that converts catalyst precursor into a halide form. A "titanating agent," as used herein, is a compound that provides the catalytically active titanium species. Halogenation and titantation convert the magnesium moiety present in the procatalyst precursor into a magnesium halide support upon which the titanium moiety (such as a titanium halide) is deposited. Not wishing to be bound by any particular theory, it is believed that during halogenation and titanation the internal electron donor (1) regulates the position of titanium on the magnesium-based support, (2) facilitates conversion of the magnesium and titanium moieties into respective halides and (3) regulates the crystallite size of the magnesium halide support during conversion. Thus, provision of the internal electron donor yields a procatalyst composition with enhanced stereoselectivity.

In an embodiment, the halogenating agent is a titanium halide having the formula $Ti(OR^e)_fX_h$ wherein $R^e$ and X are defined as above, f is an integer from 0 to 3; h is an integer from 1 to 4; and f+h is 4. In this way, the titanium halide is simultaneously the halogenating agent and the titanating agent. In an embodiment, the titanium halide is $TiCl_4$. In a further embodiment, the halogenation and the titanation are conducted in the presence of a chlorinated or a non-chlorinated aromatic liquid, such as dichlorobenzene, o-chlorotoluene, chlorobenzene, benzene, toluene, or xylene. In yet another embodiment, the halogenation and the titanation are conducted by use of a mixture of halogenating agent and chlorinated aromatic liquid comprising from 40 to 60 volume percent halogenating agent, such as $TiCl_4$.

In an embodiment, the reaction mixture is heated during halogenation. The procatalyst precursor and halogenating agent are contacted initially at a temperature from 0° C. to 60° C., or from 20° C. to 30° C., and heating is commenced at a rate of 0.1 to 10.0° C./minute, or at a rate of 1.0 to 5.0° C./minute. The internal electron donor may be added later, after an initial contact period between the halogenating agent and procatalyst precursor. Temperatures for the halogenation are from 60° C. to 150° C. (or any value or subrange therebetween), or from 90° C. to 120° C. Halogenation may be continued in the substantial absence of the internal electron donor for a period from 5 to 60 minutes, or from 10 to 50 minutes.

The manner in which the procatalyst precursor, the halogenating agent and the internal electron donor are contacted may be varied. In an embodiment, the procatalyst precursor is first contacted with a mixture containing the halogenating agent and a chlorinated aromatic compound. The resulting mixture is stirred and may be heated if desired. Next, the internal electron donor is added to the same reaction mixture without isolating or recovering of the precursor. The foregoing process may be conducted in a single reactor with addition of the various ingredients controlled by automated process control.

Contact times of the procatalyst precursor with the internal electron donor are at least 10 minutes, or at least 15 minutes, or at least 20 minutes, or at least 1 hour at a temperature from at least 25° C., or at least 50° C., or at least 60° C. up to a temperature of 150° C., or up to 120° C., or up to 115° C., or up to 110° C.

The halogenation procedure may be repeated one, two, three, or more times as desired. In an embodiment, the resulting solid material is recovered from the reaction mixture and contacted one or more times in the absence (or in the presence) of the same (or different) internal electron donor components with a mixture of the halogenating agent in the chlorinated aromatic compound for at least about 10 minutes, or at least about 15 minutes, or at least about 20 minutes, and up to about 1 hour, or up to about 45 minutes, or up to about 30 minutes, at a temperature from at least about 25° C., or at least about 50° C., or at least about 60° C., to a temperature up to about 150° C., or up to about 120° C., or up to about 115° C.

After the foregoing halogenation procedure, the resulting solid procatalyst composition is separated from the reaction medium employed in the final process, by filtering for example, to produce a moist filter cake. The moist filter cake may then be rinsed or washed with a liquid diluent to remove unreacted TiCl$_4$ and may be dried to remove residual liquid, if desired. Typically the resultant solid procatalyst composition is washed one or more times with a "wash liquid," which is a liquid hydrocarbon such as an aliphatic hydrocarbon such as isopentane, isooctane, isohexane, hexane, pentane, or octane. The solid procatalyst composition then can be separated and dried or slurried in a hydrocarbon, especially a relatively heavy hydrocarbon such as mineral oil for further storage or use.

In an embodiment, the resulting solid procatalyst composition has a titanium content of from about 0.1 percent by weight to about 6.0 percent by weight, based on the total solids weight, or from about 1.0 percent by weight to about 4.5 percent by weight, or from about 1.5 percent by weight to about 3.5 percent by weight. The weight ratio of titanium to magnesium in the solid procatalyst composition is suitably between about 1:3 and about 1:160, or between about 1:4 and about 1:50, or between about 1:6 and 1:30. In an embodiment, the internal electron donor may be present in the procatalyst composition in a molar ratio of internal electron donor to magnesium of from about 0.005:1 to about 1:1, or from about 0.01:1 to about 0.4:1. Weight percent is based on the total weight of the procatalyst composition.

In an embodiment, the procatalyst composition may be further treated by one or more of the following procedures prior to or after isolation of the solid procatalyst composition. The solid procatalyst composition may be contacted (halogenated) with a further quantity of titanium halide compound, if desired; it may be exchanged under metathesis conditions with an acid chloride, such as phthaloyl dichloride or benzoyl chloride; and it may be rinsed or washed, heat treated; or aged. The foregoing additional procedures may be combined in any order or employed separately, or not at all.

Not wishing to be bound by any particular theory, it is believed that (1) further halogenation by contacting the previously formed procatalyst composition with a titanium halide compound, especially a solution thereof in a halohydrocarbon diluent, and/or (2) further washing the previously formed procatalyst composition with a halohydrocarbon at an elevated temperature (100-150° C.), results in desirable modification of the procatalyst composition, possibly by removal of certain inactive metal compounds that are soluble in the foregoing diluent. Accordingly, in an embodiment, the procatalyst is contacted with a halogenating agent, such as a mixture of a titanium halide and a halohydrocarbon diluent, such as TiCl$_4$ and chlorobenzene, one or more times prior to isolation or recovery. In another embodiment, the procatalyst is washed at a temperature between 100 to 150° C. with chlorobenzene or o-chlorotoluene one or more times prior to isolation or recovery.

The present process for producing a procatalyst composition may comprise two or more embodiments disclosed herein.

In an embodiment, a procatalyst composition is provided which includes a combination of a magnesium moiety, a titanium moiety and an internal electron donor. The internal electron donor includes a silyl glutarate. The procatalyst composition may be produced by way of the foregoing halogenation procedure which converts the procatalyst precursor and the silyl glutarate donor into the combination of the magnesium and titanium moieties, into which the internal electron donor is incorporated. The procatalyst precursor from which the procatalyst composition is formed can be the magnesium moiety precursor, the mixed magnesium/titanium precursor, or the benzoate-containing magnesium chloride precursor.

In an embodiment, the magnesium moiety is a magnesium halide. In another embodiment, the magnesium halide is magnesium chloride, or magnesium chloride alcohol adduct.

In an embodiment, the titanium moiety is a titanium halide such as a titanium chloride. In another embodiment the titanium halide is titanium tetrachloride.

In another embodiment, the procatalyst composition includes a magnesium chloride support upon which a titanium chloride is deposited and into which the internal electron donor is incorporated.

In an embodiment, the silyl glutarate has the structure (I):

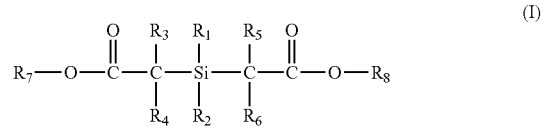

wherein $R_1$-$R_8$ are the same or different. Each of $R_1$-$R_6$ is selected from hydrogen, a substituted hydrocarbyl group having 1 to 20 carbon atoms, an unsubstituted hydrocarbyl group having 1 to 20 carbon atoms, and combinations thereof. Each of $R_7$-$R_8$ is selected from a substituted hydrocarbyl group having 1 to 20 carbon atoms and an unsubstituted hydrocarbyl group having 1 to 20 carbon atoms.

In an embodiment, two or more R groups of $R_1$-$R_8$ may be joined to form a ring structure. The ring structure may be aromatic or may be non-aromatic. The ring structure may be mono-cyclic or poly-cyclic and may be a hydrocarbyl or may include a heteroatom. Nonlimiting examples of suitable ring structures include $C_5$-$C_6$ ring structures. A nonlimiting example of a $C_5$ ring structure is a cyclopentyl group. Nonlimiting examples of suitable $C_6$ ring structures include a cyclohexyl group or a phenyl group. A nonlimiting example of a polycyclic ring structure is a fluorene-based compound.

In an embodiment, $R_1$ and $R_2$ are the same or different. Each of $R_1$ and $R_2$ is selected from hydrogen, a $C_1$-$C_6$ alkyl group, and combinations thereof. In a further embodiment, each of $R_1$ and $R_2$ is selected from a methyl group, a propyl group, an isopropyl group, a butyl group, an isobutyl group and combinations thereof.

In an embodiment, each of $R_1$ and $R_2$ is a methyl group.
In an embodiment, each of $R_1$ and $R_2$ is an isopropyl group.
In an embodiment, each of $R_1$ and $R_2$ is an isobutyl group.
In an embodiment, $R_7$ and $R_8$ are the same or different. Each of $R_7$ and $R_8$ is selected from a $C_1$-$C_6$ alkyl group.

In an embodiment, each of $R_7$ and $R_8$ is an ethyl group.
In an embodiment, $R_1$, $R_2$, $R_7$, and $R_8$ are the same or different. Each of $R_1$, $R_2$, $R_7$, and $R_8$ is selected from a $C_1$-$C_6$ alkyl group.

In an embodiment, each of $R_1$ and $R_2$ is a methyl group. Each of $R_7$ and $R_8$ is an ethyl group.
In an embodiment, each of $R_1$ and $R_2$ is an isopropyl group. Each of $R_7$ and $R_8$ is an ethyl group.
In an embodiment, each of $R_1$ and $R_2$ is an isobutyl group. Each of $R_7$ and $R_8$ is an ethyl group.

Ethoxide content in the procatalyst composition indicates the completeness of conversion of precursor metal ethoxide into a metal halide. The present internal electron donor assists in converting ethoxide into halide during halogenation. In an embodiment, the procatalyst composition includes from about 0.01 wt % to about 1.5 wt %, or from about 0.05 wt % to about 0.5 wt % ethoxide. Weight percent is based on the total weight of the procatalyst composition.

In an embodiment, the procatalyst composition includes from about 0.01 wt % to about 18 wt %, or from about 1.0 wt % to about 17 wt % silyl glutarate. Weight percent is based on the total weight of the procatalyst composition.

In an embodiment, the procatalyst composition includes from about 0.01 wt % to about 6.0 wt %, or from about 0.1 wt % to about 5.0 wt % titanium. Weight percent is based on the total weight of the procatalyst composition.

In an embodiment, the magnesium to internal electron donor molar ratio is from about 200:1 to about 1:1, or from about 100:1 to about 2:1, or from about 30:1 to about 2.5:1, or from about 20:1 to about 3:1.

In an embodiment, another procatalyst composition is provided. The procatalyst composition includes a combination of a magnesium moiety, a titanium moiety and a mixed internal electron donor. As used herein, a "mixed internal electron donor" is (i) a silyl glutarate, (ii) an electron donor component that donates a pair of electrons during production of the procatalyst composition, and (iii) optionally other components. In an embodiment, the electron donor component donates a pair of electrons during halogenation of the procatalyst precursor. In this sense, the electron donor component is an internal electron donor. In an embodiment, the electron donor component is a phthalate, ethyl benzoate, a diether and combinations thereof. The procatalyst composition with the mixed internal electron donor can be produced by way of halogenation as previously disclosed.

In an embodiment, a catalyst composition is provided. As used herein, "a catalyst composition" is a composition that forms an olefin-based polymer when contacted with an olefin under polymerization conditions. The catalyst composition includes a procatalyst composition and a cocatalyst. The procatalyst composition can be any of the foregoing procatalyst compositions containing a silyl glutarate. The catalyst composition may optionally include an external electron donor and/or an activity limiting agent.

In an embodiment, the internal electron donor of the catalyst composition is a silyl glutarate. The silyl glutarate can be any silyl glutarate as disclosed herein.

In an embodiment, the internal electron donor of the catalyst composition is a mixed internal electron donor. Nonlimiting examples of suitable mixed internal electron donors include (i) a silyl glutarate and a phthalate, (ii) a silyl glutarate and ethyl benzoate, (iii) a silyl glutarate and a diether, and combinations thereof. The silyl glutarate can be any respective silyl glutarate disclosed herein. The origin of the ethyl benzoate can be from (i) the procatalyst precursor, (ii) the internal electron donor, (iii) addition of ethyl benzoate during halogenation, and (iv) any combination of (i)-(iii).

The catalyst composition includes a cocatalyst. As used herein, a "cocatalyst" is a substance capable of converting the procatalyst to an active polymerization catalyst. The cocatalyst may include hydrides, alkyls, or aryls of aluminum, lithium, zinc, tin, cadmium, beryllium, magnesium, and combinations thereof. In an embodiment, the cocatalyst is a hydrocarbyl aluminum cocatalyst represented by the formula $R_3Al$ wherein each R is an alkyl, cycloalkyl, aryl, or hydride radical; at least one R is a hydrocarbyl radical; two or three R radicals can be joined in a cyclic radical forming a heterocyclic structure; each R can be the same or different; and each R, which is a hydrocarbyl radical, has 1 to 20 carbon atoms, and preferably 1 to 10 carbon atoms. In a further embodiment, each alkyl radical can be straight or branched chain and such hydrocarbyl radical can be a mixed radical, i.e., the radical can contain alkyl, aryl, and/or cycloalkyl groups. Nonlimiting examples of suitable radicals are: methyl, ethyl, propyl, isopropyl, butyl, isobutyl, tert-butyl, pentyl, neopentyl, hexyl, 2-methylpentyl, heptyl, octyl, isooctyl, 2-ethylhexyl, 5,5-dimethylhexyl, nonyl, decyl, isodecyl, undecyl, dodecyl, phenyl, phenethyl, methoxyphenyl, benzyl, tolyl, xylyl, naphthyl, naphthal, methylnapthyl, cyclohexyl, cycloheptyl, and cyclooctyl.

Nonlimiting examples of suitable hydrocarbyl aluminum compounds are as follows: triisobutylaluminum, trihexylaluminum, di-isobutylaluminum hydride, dihexylaluminum hydride, isobutylaluminum dihydride, hexylaluminum dihydride, di-isobutylhexylaluminum, isobutyl dihexylaluminum, trimethylaluminum, triethylaluminum, tripropylaluminum, triisopropylaluminum, tri-n-butylaluminum, trioctylaluminum, tridecylaluminum, tridodecylaluminum, tribenzylaluminum, triphenylaluminum, trinaphthylaluminum, and tritolylaluminum. In an embodiment, the cocatalyst is selected from triethylaluminum, triisobutylaluminum, trihexylaluminum, di-isobutylaluminum hydride, and dihexylaluminum hydride.

In an embodiment, the cocatalyst is a hydrocarbyl aluminum compound represented by the formula $R_nAlX_{3-n}$ wherein n=1 or 2, R is an alkyl, and X is a halide or alkoxide. Nonlimiting examples of suitable compounds are as follows: methylaluminoxane, isobutylaluminoxane, diethylaluminum ethoxide, diisobutylaluminum chloride, tetraethyldialuminoxane, tetraisobutyldialuminoxane, diethylaluminum chloride, ethylaluminum dichloride, methylaluminum dichloride, and dimethylaluminum chloride.

In an embodiment, the cocatalyst is triethylaluminum. The molar ratio of aluminum to titanium is from about 5:1 to about 500:1, or from about 10:1 to about 200:1, or from about 15:1 to about 150:1, or from about 20:1 to about 100:1. In another embodiment, the molar ratio of aluminum to titanium is about 45:1.

In an embodiment, the present catalyst composition includes an external electron donor. As used herein, an "external electron donor" (or "EED") is a compound added independent of procatalyst formation and includes at least one functional group that is capable of donating a pair of electrons to a metal atom. A "mixed external electron donor" (or "MEED") is a mixture of two or more external electron donors. Bounded by no particular theory, it is believed that provision of one or more external electron donors in the catalyst composition affects the following properties of the formant polymer: level of tacticity (i.e., xylene soluble material), molecular weight (i.e., melt flow), molecular weight distribution (MWD), melting point, and/or oligomer level.

In an embodiment, the external electron donor may be selected from one or more of the following: a silicon compound, an amine, an ether, a carboxylate, a ketone, an amide, a carbamate, a phosphine, a phosphate, a phosphite, a sulfonate, a sulfone, and/or a sulfoxide. Nonlimiting examples of suitable compounds for the EED include silicon compounds, such as alkoxysilanes; ethers and polyethers, such as alkyl-, cycloalkyl-, aryl-, mixed alkyl/aryl-, mixed alkyl/cycloalkyl-, and/or mixed cycloalkyl/aryl-ethers and/or polyethers; esters and polyesters, especially alkyl, cycloalkyl- and/or aryl-esters of monocarboxylic or dicarboxylic acids, such as aromatic monocarboxylic- or dicarboxylic-acids; alkyl- or cycloalkyl-ether or thioether derivatives of such esters or polyesters, such as alkyl ether derivatives of alkyl esters or diesters of aromatic monocarboxylic or dicarboxylic acids; and Group 15 or 16 heteroatom-substituted derivatives of all of the foregoing; and amine compounds, such as cyclic, aliphatic or aromatic amines, more especially pyrrole or pyridine compounds; all of the foregoing EED's containing from 2 to 60 carbons total and from 1 to 20 carbons in any alkyl or alkylene group, 3 to 20 carbons in any cycloalkyl or cycloalkylene group, and 6 to 20 carbons in any aryl or arylene group.

In an embodiment, the EED may be a silicon compound having the general formula (II):

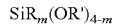

$SiR_m(OR')_{4-m}$ wherein R independently each occurrence is hydrogen or a hydrocarbyl or an amino group, optionally substituted with one or more substituents containing one or more Group 14, 15, 16, or 17 heteroatoms. R contains up to 20 atoms not counting hydrogen and halogen. R' is a $C_{1-20}$ alkyl group, and m is 0, 1, or 2. In an embodiment, R is $C_{6-12}$ aryl, alkyl or aralkyl, $C_{3-12}$ cycloallyl, $C_{3-12}$ branched alkyl, or $C_{3-12}$ cyclic amino group, R' is $C_{1-4}$ alkyl, and m is 1 or 2.

le;.5qIn an embodiment, the EED includes a silicon compound selected from one or more or the following: a dimethoxysilane; a dimethoxysilane having at least one secondary alkyl and/or a secondary amino group directly bonded to the silicon atom; a dimethoxysilane containing two linear alkyl groups; a dimethoxysilane containing two alkenyl groups or hydrogen, wherein one or more hydrogen atoms may be substituted by a halogen; a dimethoxysilane containing two alkenyl groups, a diether, and/or a dialkoxybenzene; a trimethoxysilane; a diethoxysilane; a triethoxysilane; a tetraethoxysilane; and any combination thereof.

Nonlimiting examples of suitable silicon compounds for the EED include dicyclopentyldimethoxysilane, di-tert-butyldimethoxysilane, methylcyclohexyldimethoxysilane, ethylcyclohexyldimethoxysilane, diphenyldimethoxysilane, diisopropyldimethoxysilane, diisobutyldiethoxysilane, isobutylisopropyldimethoxysilane, di-n-butyldimethoxysilane, cyclopentyltrimethoxysilane, isopropyltrimethoxysilane, n-propyldimethoxysilane, n-propyltriethoxysilane, ethyltriethoxysilane, diethylaminotriethoxysilane, isobutylisopropyldiethoxysilane, diisobutyldimethoxysilane, t-butylisopropyldimethoxysilane, cyclopentylpyrrolidinodimethoxysilane, bis(pyrrolidino)dimethoxysilane, bis(perhydroisoquinolino)dimethoxysilane, dimethyldimethoxysilane, vinylmethyldimethoxysilane, n-octylmethyldimethoxysilane, n-octadecylmethyldimethoxysilane, methyldimethoxysilane, 3-chloropropylmethyldimethoxysilane, 2-chloroethylmethyldimethoxysilane, allyldimethoxysilane, (3,3,3-trifluoropropyl)methyldimethoxysilane, n-propylmethyldimethoxysilane, chloromethylmethyldimethoxysilane, di-n-octyldimethoxysilane, vinyl(chloromethyl)dimethoxysilane, methylcyclohexyldiethoxysilane, vinylmethyldiethoxysilane, 1-(triethoxysilyl)-2-(diethoxymethylsilyl)ethane, n-octylmethyldiethoxysilane, octaethoxy-1,3,5-trisilapentane, n-octadecylmethyldiethoxysilane, methacryloxypropylmethyldiethoxysilane, 2-hydroxy-4-(3-methyldiethoxysilylpropoxy)diphenylketone, (3-glycidoxypropyl)methyldiethoxysilane, dodecylmethyldiethoxysilane, dimethyldiethoxysilane, diethyldiethoxysilane, 1,1-diethoxy-1-silacyclopent-3-ene, chloromethylmethyldiethoxysilane, bis(methyldiethoxysilylpropyl)amine, 3-aminopropylmethyldiethoxysilane, (methacryloxymethyl)methyldiethoxysilane, 1,2-bis(methyldiethoxysilyl)ethane, vinyltrimethoxysilane, vinyltriethoxysilane, benzyltriethoxysilane, butenyltriethoxysilane, (triethoxysilyl)cyclohexane, O-(vinyloxybutyl)-N-triethoxysilylpropylcarbamate, 10-undecenyltrimethoxysi lane, n-(3-trimethoxysilylpropyl)pyrrole, N-[5-(trimethoxysilyl)-2-aza-1-oxopentyl]caprolactam, (3,3,3-trifluoropropyl)trimethoxysilane, triethoxysilylundecanal ethylene glycol acetal, (S)-N-triethoxysilylpropyl-O-menthocarbamate, triethoxysilylpropylethylcarbamate, N-(3-triethoxysilylpropyl)-4,5-dihydroimidazole, (3-triethoxysilylpropyl)-t-butylcarbamate, styrylethyltrimethoxysilane, 2-(4-pyridylethyl)triethoxysilane, (S)-N-1-phenylethyl-N'-triethoxysilylpropylurea, (R)-N-1-phenylethyl-N'-triethoxysilylpropylurea, N-phenylaminopropyltrimethoxysilane, N-phenylaminomethyltriethoxysilane, phenethyltrimethoxysilane, pentyltriethoxysilane, n-octyltrimethoxysilane, n-octyltriethoxysilane, 7-octenyltrimethoxysilane, S-(octanoyl)mercaptopropyltriethoxysilane, n-octadecyltrimethoxysilane, n-octadecyltriethoxysilane, methyltrimethoxysilane, methyltriethoxysilane, N-methylaminopropyltrimethoxysilane, 3-methoxypropyltrimethoxysilane, methacryloxypropyltrimethoxysilane, methacryloxypropyltriethoxysilane, methacryloxymethyltrimethoxysilane, methacryloxymethyltriethoxysilane, and O-(methacryloxyethyl)-N-(triethoxysilylpropyl)carbamate, tetramethoxysilane, tetraethoxysilane, methylcyclohexyldiethoxysilane, di-isobutyldiethoxysilane, tetraethoxysilane, benzyltriethoxysilane, but-3-enyltriethoxysilane, 1-(triethoxysilyl)-2-pentene, (triethoxysilyl)cyclohexane, and any combination of the foregoing.

In an embodiment, the EED may be a diether, a dimer of a diether, a dialkoxybenzene, a dimer of a dialkoxybenzene, a dialkoxybenzene linked by a linear hydrocarbon group, and any combination thereof. It is noted that the diethers for the ALA set forth below apply equally as nonlimiting examples for the EED diether.

In an embodiment, the external electron donor can be a mixture of at least 2 silicon compounds (i.e., a MEED). In a further embodiment, the mixture can be dicyclopentyldimethoxysilane and methylcyclohexyldimethoxysilane, dicyclopentyldimethoxysilane and tetraethoxysilane, or dicyclopentyldimethoxysilane and n-propyltriethoxysilane.

In an embodiment, the EED includes dicyclopentyldimethoxysilane.

In an embodiment, the external electron donor is selected from one or more of the following: a benzoate, a succinate, and/or a diol ester.

In an embodiment, the external electron donor includes 2,2,6,6-tetramethylpiperidine.

It is understood that the EED may comprise any of the foregoing EED compounds. It is further understood that the EED may be a MEED which may comprise two or more of any of the foregoing EED compounds.

In an embodiment, the catalyst composition includes an activity limiting agent (ALA). As used herein, an "activity limiting agent" ("ALA") is a material that reduces catalyst activity at elevated temperature (i.e., temperature greater than about 85° C.). An ALA inhibits or otherwise prevents polymerization reactor upset and ensures continuity of the polymerization process. Typically, the activity of Ziegler-Natta catalysts increases as the reactor temperature rises. Ziegler-Natta catalysts also typically maintain high activity near the melting point temperature of the polymer produced. The heat generated by the exothermic polymerization reaction may cause polymer particles to form agglomerates and may ultimately lead to disruption of continuity for the polymer production process. The ALA reduces catalyst activity at elevated temperature, thereby preventing reactor upset, reducing (or preventing) particle agglomeration, and ensuring continuity of the polymerization process.

The activity limiting agent may be a carboxylic acid ester, a diether, a diol ester, and combinations thereof. The carboxylic acid ester can be an aliphatic or aromatic, mono- or polycarboxylic acid ester. Nonlimiting examples of suitable monocarboxylic acid esters include ethyl and methyl benzoate, p-methoxy ethyl benzoate, p-ethoxy methyl benzoate, p-ethoxy ethyl benzoate, ethyl acrylate, methyl methacrylate, ethyl acetate, p-chloro ethyl benzoate, p-amino hexyl benzoate, isopropyl naphthenate, n-amyl toluate, ethyl cyclohexanoate and propyl pivalate.

Nonlimiting examples of suitable polycarboxylic acid esters include dimethyl phthalate, diethyl phthalate, di-n-propyl phthalate, diisopropyl phthalate, di-n-butyl phthalate, diisobutyl phthalate, di-tert-butyl phthalate, diisoamyl phthalate, di-tert-amyl phthalate, dineopentyl phthalate, di-2-ethylhexyl phthalate, and di-2-ethyldecyl phthalate.

The aliphatic carboxylic acid ester may be a $C_4$-$C_{30}$ aliphatic acid ester, may be a mono- or a poly- (two or more) ester, may be straight chain or branched, may be saturated or unsaturated, and any combination thereof. The $C_4$-$C_{30}$ aliphatic acid ester may also be substituted with one or more Group 14, 15 or 16 heteroatom containing substituents. Nonlimiting examples of suitable $C_4$-$C_{30}$ aliphatic acid esters include $C_{1-20}$ alkyl esters of aliphatic $C_{4-30}$ monocarboxylic acids, $C_{1-20}$ alkyl esters of aliphatic $C_{8-20}$ monocarboxylic acids, $C_{1-4}$ alkyl mono- and diesters of aliphatic $C_{4-20}$ monocarboxylic acids and dicarboxylic acids, $C_{1-4}$ alkyl esters of aliphatic $C_{8-20}$ monocarboxylic acids and dicarboxylic acids, and $C_{4-20}$ mono- or polycarboxylate derivatives of $C_{2-100}$ (poly)glycols or $C_{2-100}$ (poly)glycol ethers. In a further embodiment, the $C_4$-$C_{30}$ aliphatic acid ester may be isopropyl myristate, di-n-butyl sebacate, (poly)(alkylene glycol) mono- or diacetates, (poly)(alkylene glycol) mono- or di-myristates, (poly)(alkylene glycol) mono- or di-laurates, (poly)(alkylene glycol) mono- or di-oleates, glyceryl tri(acetate), glyceryl tri-ester of $C_{2-40}$ aliphatic carboxylic acids, and mixtures thereof. In a further embodiment, the $C_4$-$C_{30}$ aliphatic ester is isopropyl myristate or di-n-butyl sebacate.

In an embodiment, the activity limiting agent includes a diether. The diether can be a 1,3-diether compound represented by the following structure (III):

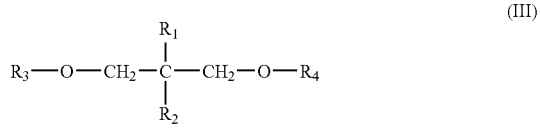

wherein $R_1$ to $R_4$ are independently of one another an alkyl, aryl or aralkyl group having up to 20 carbon atoms, which may optionally contain a group 14, 15, 16, or 17 heteroatom, and $R_1$ and $R_2$ may be a hydrogen atom. The diether may be linear or branched, and may include one or more of the following groups: alkyl, cycloaliphatic, aryl, alkylaryl or arylalkyl radicals with 1-18 carbon atoms, and hydrogen. $R_1$ and $R_2$ may be linked to form a cyclic structure, such as cyclopentadiene or fluorene.

In an embodiment, the activity limiting agent includes a succinate composition having the following structure (IV):

wherein R and R' may be the same or different, R and/or R' including one or more of the following groups: linear or branched alkyl, alkenyl, cycloalkyl, aryl, arylalkyl or alkylaryl group, optionally containing heteroatoms. One or more ring structures can be formed via one or both 2- and 3-position carbon atom.

In an embodiment, the activity limiting agent includes a diol ester as represented by the following structure (V):

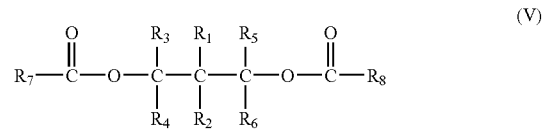

$R_1$ and $R_2$, may be the same or different, and each may be selected from hydrogen, methyl, ethyl, n-propyl, i-propyl, n-butyl, i-butyl, t-butyl, allyl, phenyl, or halophenyl group. $R_3$, $R_4$, $R_5$, $R_6$, $R_7$, and $R_8$, may be the same or different, and each may be selected from halogen, substituted, or unsubstituted hydrocarbyl having 1 to 20 carbon atoms. $R_3$, $R_4$, $R_5$, and $R_6$ may also be hydrogen. $R_1$-$R_6$ groups may optionally contain one or more heteroatoms replacing carbon, hydrogen or both, the hetero-atom selected from nitrogen, oxygen, sulfur, silicon, phosphorus and a halogen. $R_7$ and $R_8$, may be the same or different, and may be an aliphatic hydrocarbyl group or an aromatic hydrocarbyl group.

In an embodiment, the external electron donor and/or activity limiting agent can be added into the reactor separately. In another embodiment, the external donor and the activity limiting agent can be mixed together in advance and then added to the catalyst composition and/or into the reactor as a mixture. In the mixture, more than one external donor or more than one activity limiting agent can be used. In an embodiment, the mixture is dicyclopentyldimethoxysilane and isopropyl myristate, dicyclopentyldimethoxysilane and poly(ethylene glycol) laurate, dicyclopentyldimethoxysilane and isopropyl myristate and poly(ethylene glycol) dioleate, methylcyclohexyldimethoxysilane and isopropyl myristate, n-propyltrimethoxysilane and isopropyl myristate, dimethyldimethoxysilane and methylcyclohexyldimethoxysilane and isopropyl myristate, dicyclopentyldimethoxysilane and n-propyltriethoxysilane and isopropyl myristate, and dicyclopentyldimethoxysilane and tetraethoxysilane and isopropyl myristate and combinations thereof.

In an embodiment, the catalyst composition includes any of the foregoing external electron donors in combination with any of the foregoing activity limiting agents.

The present catalyst composition may comprise two or more embodiments disclosed herein.

In an embodiment, a process for producing an olefin-based polymer is provided. The process includes contacting an olefin with a catalyst composition under polymerization conditions. The catalyst composition includes a silyl glutarate. The silyl glutarate can be any silyl glutarate as disclosed herein. The process further includes forming an olefin-based polymer.

In an embodiment, the catalyst composition includes a procatalyst composition and a cocatalyst. The procatalyst composition may be any procatalyst composition as disclosed herein. The procatalyst composition may include a silyl glutarate as the internal electron donor or a mixed internal electron donor as disclosed herein. The cocatalyst may be any cocatalyst as disclosed herein. The catalyst composition may optionally include an external electron donor and/or an activity limiting agent as previously disclosed.

In an embodiment, the olefin-based polymer can be a propylene-based olefin, an ethylene-based olefin, and combinations thereof. In an embodiment, the olefin-based polymer is a propylene-based olefin.

One or more olefin monomers can be introduced in a polymerization reactor to react with the catalyst and to form a polymer (or a fluidized bed of polymer particles). Nonlimiting examples of suitable olefin monomers include ethylene, propylene, $C_{4-20}$ α-olefins, such as 1-butene, 1-pentene, 1-hexene, 4-methyl-1-pentene, 1-heptene, 1-octene, 1-decene, 1-dodecene and the like; $C_{4-20}$ diolefins, such as 1,3-butadiene, 1,3-pentadiene, norbornadiene, 5-ethylidene-2-norbornene (ENB) and dicyclopentadiene; $C_{8-40}$ vinyl aromatic compounds including styrene, o-, m-, and p-methylstyrene, divinylbenzene, vinylbiphenyl, vinylnapthalene; and halogen-substituted $C_{8-40}$ vinyl aromatic compounds such as chlorostyrene and fluorostyrene.

As used herein, "polymerization conditions" are temperature and pressure parameters within a polymerization reactor suitable for promoting polymerization between the catalyst composition and an olefin to form the desired polymer. The polymerization process may be a gas phase, a slurry, or a bulk polymerization process, operating in one, or more than one, polymerization reactor. Accordingly, the polymerization reactor may be a gas phase polymerization reactor, a liquid-phase polymerization reactor, or a combination thereof.

It is understood that provision of hydrogen in the polymerization reactor is a component of the polymerization conditions. During polymerization, hydrogen is a chain transfer agent and affects the molecular weight (and correspondingly the melt flow rate) of the resultant polymer.

In an embodiment, polymerization occurs by way of gas phase polymerization. As used herein, "gas phase polymerization" is the passage of an ascending fluidizing medium, the fluidizing medium containing one or more monomers, in the presence of a catalyst through a fluidized bed of polymer particles maintained in a fluidized state by the fluidizing medium. "Fluidization," "fluidized," or "fluidizing" is a gas-solid contacting process in which a bed of finely divided polymer particles is lifted and agitated by a rising stream of gas. Fluidization occurs in a bed of particulates when an upward flow of fluid through the interstices of the bed of particles attains a pressure differential and frictional resistance increment exceeding particulate weight. Thus, a "fluidized bed" is a plurality of polymer particles suspended in a fluidized state by a stream of a fluidizing medium. A "fluidizing medium" is one or more olefin gases, optionally a carrier gas (such as $H_2$ or $N_2$) and optionally a liquid (such as a hydrocarbon) which ascends through the gas-phase reactor.

A typical gas-phase polymerization reactor (or gas phase reactor) includes a vessel (i.e., the reactor), the fluidized bed, a distribution plate, inlet and outlet piping, a compressor, a cycle gas cooler or heat exchanger, and a product discharge system. The vessel includes a reaction zone and a velocity reduction zone, each of which is located above the distribution plate. The bed is located in the reaction zone. In an embodiment, the fluidizing medium includes propylene gas and at least one other gas such as an olefin and/or a carrier gas such as hydrogen or nitrogen.

In an embodiment, the contacting occurs by way of feeding the catalyst composition into the polymerization reactor and introducing the olefin into the polymerization reactor. In an embodiment, the process includes contacting the olefin with a cocatalyst. The cocatalyst can be mixed with the procatalyst composition (pre-mix) prior to the introduction of the procatalyst composition into the polymerization reactor. In another embodiment, cocatalyst is added to the polymerization reactor independently of the procatalyst composition. The independent introduction of the cocatalyst into the polymerization reactor can occur simultaneously, or substantially simultaneously, with the procatalyst composition feed.

In an embodiment, the process includes mixing the external electron donor (and optionally the activity limiting agent) with the procatalyst composition. The external electron donor can be complexed with the cocatalyst and mixed with the procatalyst composition (pre-mix) prior to contact between the catalyst composition and the olefin. In another embodiment, the external electron donor and/or the activity limiting agent can be added independently to the polymerization reactor. In an embodiment, the external electron donor is dicyclopentyldimethoxysilane or n-propyltrimethoxysilane.

In another embodiment, the catalyst composition includes dicyclopentyldimethoxysilane and/or n-propyltrimethoxysilane and an activity limiting agent such as isopropyl myristate.

In an embodiment, a polypropylene homopolymer is produced in a first reactor. The content of the first reactor is subsequently transferred to a second reactor into which ethylene is introduced. This results in production of a propylene-ethylene copolymer in the second reactor.

In an embodiment, a polypropylene homopolymer is formed via introduction of propylene and any of the present procatalyst compositions, cocatalysts, external electron donors, and activity limiting agents in the first reactor. The polypropylene homopolymer is introduced into the second reactor along with ethylene and an external electron donor and optionally an activity limiting agent. The external electron donor and the activity limiting agent may be the same as or different from the respective components used in the first reactor. This produces a propylene-ethylene copolymer in the second reactor.

In an embodiment, the olefin is propylene. The process includes forming a propylene-based polymer having a melt flow rate (MFR) from about 0.01 g/10 min to about 800 g/10 min, or from about 0.1 g/10 min to about 200 g/10 min, or from about 0.5 g/10 min to about 150 g/10 min. In a further embodiment, the propylene-based polymer is a polypropylene homopolymer.

In an embodiment, the olefin is propylene. The process includes forming a propylene-based polymer having a xylene solubles content from about 0.5% to about 10%, or from about 1% to about 8%, or from about 1% to about 4%. In a further embodiment, the propylene-based polymer is a polypropylene homopolymer.

In an embodiment, the olefin is propylene. The process includes forming a propylene-based polymer having a polydispersity index (PDI) from about 2 to about 20, or from about 3 to about 10, or from about 3 to about 8. In a further embodiment, the propylene-based polymer is a polypropylene homopolymer.

The present polymerization process may comprise two or more embodiments disclosed herein.

Not wishing to be bound by any particular theory, it is believed that the present catalyst compositions with silyl glutarate internal electron donor yield olefin-based polymers with high catalyst activity, and selectivity when compared to catalyst compositions made from a similar procatalyst precursor and another internal electron donor.

Definitions

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range. Numerical ranges have been recited, as discussed herein, reference melt index, melt flow rate, and other properties.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition," as used herein, includes a mixture of materials which comprise the composition, as well as reaction products and decomposition products formed from the materials of the composition.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term "interpolymer," as used herein, refers to polymers prepared by the polymerization of at least two different types of monomers. The generic term interpolymer thus includes copolymers, usually employed to refer to polymers prepared from two different monomers, and polymers prepared from more than two different types of monomers.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term, "ethylene-based polymer," as used herein, refers to a polymer that comprises a majority weight percent polymerized ethylene monomer (based on the total weight of polymerizable monomers), and optionally may comprise at least one polymerized comonomer.

The term, "ethylene/α-olefin interpolymer," as used herein, refers to an interpolymer that comprises a majority weight percent polymerized ethylene monomer (based on the total amount of polymerizable monomers), and at least one polymerized α-olefin.

The term, "propylene-based polymer," as used herein, refers to a polymer that comprises a majority weight percent polymerized propylene monomer (based on the total amount of polymerizable monomers), and optionally may comprise at least one polymerized comonomer.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 and 20 carbon atoms.

The term "substituted alkyl," as used herein, refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, alkylhalo, hydroxy, phosphido, alkoxy, amino, thio, nitro, and combinations thereof. Suitable substituted alkyls include, for example, benzyl, trifluoromethyl and the like.

The term "aryl," as used herein, refers to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. The aryls have 6 and 20 carbon atoms.

Test Methods

Flexural modulus is determined in accordance with ASTM D790-00.

Melt flow rate (MFR) is measured in accordance with ASTM D 1238-01 test method at 230° C. with a 2.16 kg weight for propylene-based polymers.

Melt index for the ethylene-based polymers is measured in accordance with ASTM D 1238-01 test method at 190° C. with a 2.16 kg weight for ethylene-based polymers.

Xylene Solubles (XS) is the weight percent of resin that stays in the solution after the resin is dissolved in hot xylene and the solution is allowed to cool to 23° C. XS is measured using a $^1$H NMR method as described in U.S. Pat. No. 5,539,309, the entire content of which is incorporated herein by reference.

Polydispersity Index (PDI) is measured by an AR-G2 rheometer which is a stress control dynamic spectrometer manufactured by TA Instruments using a method according to Zeichner G R, Patel P D (1981) "A comprehensive Study of Polypropylene Melt Rheology" Proc. of the 2$^{nd}$ World Congress of Chemical Eng., Montreal, Canada. An ETC oven is used to control the temperature at 180° C.±0.1° C. Plant nitrogen purged inside the oven to keep sample from degradation by oxygen and moisture. A pair of 25 mm in diameter cone and plate sample holder is used. Samples are compress molded into 50 mm×100 mm×2 mm plaque. Samples are cut into 19 mm square and loaded on the center of the bottom plate. The geometries of upper cone is (1) Cone angle: 5:42:20 (deg:min:sec); (2) Diameter: 25 mm; (3) Truncation gap: 149 micron. The geometry of the bottom plate is 25 mm cylinder. Testing procedure:

- The cone & plate sample holder are heated in the ETC oven at 180° C. for 2 hours. Then the gap is zeroed under blanket of nitrogen gas.
- Cone is raised to 2.5 mm and sample loaded unto the top of the bottom plate.
- Start timing for 2 minutes.
- The upper cone is immediately lowered to slightly rest on top of the sample by observing the normal force.
- After two minutes the sample is squeezed down to 165 micron gap by lower the upper cone.
- The normal force is observed when the normal force down to <0.05 Newton the excess sample is removed from the edge of the cone and plate sample holder by a spatula.
- The upper cone is lowered again to the truncation gap which is 149 micron.
- An Oscillatory Frequency Sweep test is performed under these conditions:
  i. Test delayed at 180° C. for 5 minutes.
  ii. Frequencies: 628.3 r/s to 0.1 r/s.
  iii. Data acquisition rate: 5 point/decade.
  iv. Strain: 10%
- When the test is completed the crossover modulus (Gc) is detected by the Rheology Advantage Data Analysis program furnished by TA Instruments.
- PDI=100,000 Gc (in Pa units).

Final melting point ($T_{MF}$) is the temperature to melt the most perfect crystal in the sample and is regarded as a measure of isotacticity and inherent polymer crystallizability. The test is conducted using a TA Q100 Differential Scanning Calorimeter. A sample is heated from 0° C. to 240° C. at a rate of 80° C./min, cooled at the same rate to 0° C., then heated again at the same rate up to 150° C., held at 150° C. for 5 minutes and then heated from 150° C. to 180° C. at 1.25° C./min. The $T_{MF}$ is determined from this last cycle by calculating the onset of the baseline at the end of the heating curve.

Testing Procedure:
(1) Calibrate instrument with high purity indium as standard.
(2) Purge the instrument head/cell with a constant 50 ml/min flow rate of nitrogen constantly.
(3) Sample preparation:
Compression mold 1.5 g of powder sample using a 30-G302H-18-CX Wabash Compression Molder (30 ton): (a) heat mixture at 230° C. for 2 minutes at contact; (b) compress the sample at the same temperature with 20 ton pressure for 1 minute; (c) cool the sample to 45° F. and hold for 2 minutes with 20 ton pressure; (d) cut the plaque into 4 of about the same size, stack them together, and repeat steps (a)-(c) in order to homogenize sample.
(4) Weigh a piece of sample (preferably between 5 to 8 mg) from the sample plaque and seal it in a standard aluminum sample pan. Place the sealed pan containing the sample on the sample side of the instrument head/cell and place an empty sealed pan in the reference side. If using the auto sampler, weigh out several different sample specimens and set up the machine for a sequence.
(5) Measurements:
(i) Data storage: off
(ii) Ramp 80.00° C./min to 240.00° C.
(iii) Isothermal for 1.00 min
(iv) Ramp 80.00° C./min to 0.00° C.
(v) Isothermal for 1.00 min
(vi) Ramp 80.00° C./min to 150.00° C.
(vii) Isothermal for 5.00 min
(viii) Data storage: on
(ix) Ramp 1.25° C./min to 180.00° C.
(x) End of method
(6) Calculation: $T_{MF}$ is determined by the interception of two lines. Draw one line from the base-line of high temperature. Draw another line from through the deflection of the curve close to the end of the curve at high temperature side.

By way of example and not by limitation, examples of the present disclosure will now be provided.

EXAMPLES

1. Synthesis of Silyl Glutarate

Diethyl 2,2'-(diisopropylsilanediyl)diacetate

Diisopropylsilanediyl bis(trifluoromethanesulfonate): An oven-dried 100 mL-RB flask is charged with dichlorodiisopropylsilane (9.2 g, 0.05 mol). Then 15 g of trifluoromethanesulfonic acid (15 g, 0.10 mol) is added dropwise. The mixture is heated at 60° C. until no further HCl evolves. The residue is distilled to yield 12 g (60%) of the product as clear liquid. $^1$H NMR (500 MHz, CDCl$_3$, in ppm) δ 1.58 (heptet, 2H, J=7.2 Hz), 1.24 (d, 12H, J=7.2 Hz).

Diethyl 2,2'-(diisopropylsilanediyl)diacetate: A dry-ice-acetone cooled 250 mL-RB flask is charged with anhydrous THF (30 ml) and diisopropylamine (2.2 g, 0.022 mol). A solution of butyl lithium in hexanes (1.6 M, 16 ml, 0.025 mol) is added over 30 minutes. After stirring at −78° C. for an additional 30 minutes, the mixture is warmed up to 0° C. and stirred for an hour. The mixture is cooled again in a dry-ice-acetone bath, and anhydrous ethyl acetate (1.76 g, 0.02 mol) is added dropwise over 30 minutes. After the mixture is stirred at −78° C. for 30 minutes, diisopropylsilanediyl bis(trifluoromethanesulfonate) (4.12 g, 0.01 mol) is added dropwise over 10 minutes. The reaction is quenched with water, and poured into ice-water. The organic layer is separated, and the aqueous layer is extracted with ether. The combined organic solution is washed with brine, dried over sodium sulfate, filtered, and the filtrate concentrated. The residue is purified by distillation in a Kugelrohr to yield 1.15 g (40%) of product as a yellowish oil. $^1$H NMR (500 MHz, CDCl$_3$, in ppm) δ 4.09 (q, 4H, J=7.0 Hz), 1.99 (s, 4H), 1.24 (t, 6H, J=7.0 Hz), 1.12 (heptet, 2H, J=6.5 Hz), 1.06 (d, 12H, J=6.5 Hz).

Diethyl 2,2'-(dimethylsilanediyl)diacetate

Dimethylsilanediyl bis(trifluoromethanesulfonate): An oven-dried 100 mL-RB flask is charged with dichlorodimethylsilane (6.45 g, 0.05 mol). Then trifluoromethanesulfonic acid (15 g, 0.10 mol) is added dropwise. The mixture is heated at 60° C. until no HCl evolves. The residue is distilled to yield 10.7 g (60%) of the product as a clear liquid. $^1$H NMR (500 MHz, CDCl$_3$, in ppm) δ 0.88 (s, 6H).

Diethyl 2,2'-(dimethylsilanediyl)diacetate: An oven-dried 100 mL-RB flask is charged with ethyl acetate (5.3 g, 0.06 mol), and triethylamine (6.1 g, 0.06 mol). The flask is then cooled in an ice-water bath, and dimethylsilanediyl bis(trifluoromethanesulfonate) (10.7 g, 0.03 mol) is added dropwise. After stirring at 0° C. for 1 h, the mixture is warmed up to room temperature and stirred overnight. The mixture is poured into ice-water and then extracted with diethyl ether. The combined ether extract is washed with brine and dried over sodium sulfate. After filtration, the filtrate is concentrated and the residue is distilled in a Kugelrohr to yield 1.6 g (23%) of the product as a light-yellowish oil. $^1$H NMR (500 MHz, CDCl$_3$, in ppm) δ 4.10 (q, 4H, J=7.5 Hz), 1.99 (s, 4H), 1.24 (t, 6H, J=7.5 Hz), 0.22 (s, 6H).

Diethyl 2,2'-(diisobutylsilanediyl)diacetate

Diisobutylsilanediyl bis(trifluoromethanesulfonate): An oven-dried 250 mL-RB flask is charged with diisobutylchlorosilane (17.9 g, 0.10 mol). Then trifluoromethanesulfonic acid (45 g, 0.30 mol) is added dropwise. The mixture is heated at 60° C. until no HCl evolves (about 6 hours). The residue is distilled to yield 32 g (73%) of the product as a clear liquid. $^1$H NMR (500 MHz, CDCl$_3$, in ppm) δ 2.06 (theptat, 2H, J=6.5 Hz, 7.0 Hz), 1.26 (d, 4H, J=7.0 Hz), 1.09 (d, 6H, J=6.5 Hz).

Diethyl 2,2'-(diisobutylsilanediyl)diacetate: A dry-ice-acetone cooled 500 mL-RB flask is charged with anhydrous THF (90 ml) and diisopropylamine (6.7 g, 0.066 mol). A solution of butyl lithium in hexanes (1.6 M, 48 ml, 0.075 mol) is added over 1 hour. After stirring at −78° C. for an additional 30 minutes, the mixture is warmed to 0° C. and stirred for an hour and at room temperature for 15 minutes. The mixture is cooled again in a dry-ice acetone bath, and anhydrous ethyl acetate (5.28 g, 0.06 mol) is added dropwise over 30 minutes. After the mixture is stirred at −78° C. for 1 hour, diisobutylsilanediyl bis(trifluoromethanesulfonate) (14.4 g, 0.01 mol) is added dropwise over 30 minutes. After about 4 hours, the reaction is quenched with water, and poured into ice-water. The organic layer is separated, and the aqueous layer is extracted with ether. The combined organic solution is washed with brine, dried over sodium sulfate, filtered, and the filtrate concentrated. The residue is purified by flash column chromatography on silica gel yield 2.6 g (27%) of product as a yellowish oil. $^1$H NMR (500 MHz, CDCl$_3$, in ppm) δ 4.10 (q, 4H, J=7.0 Hz), 2.03 (s, 4H), 1.82-1.92 (theptat, 2H, J=6.5 Hz, 6.5 Hz), 1.25 (t, 6H, J=7.0 Hz), 0.96 (d, 12H, J=6.5 Hz), 0.75 (d, 4H, J=6.5 Hz).

The compounds produced by way of the foregoing procedures are provided in Table 1 below.

TABLE 1

| Compound | Structure | $^1$H NMR (500 MHz, CDCl$_3$, ppm) |
|---|---|---|
| Diethyl 2,2'-(diisopropylsilanediyl)diacetate (IED1) | 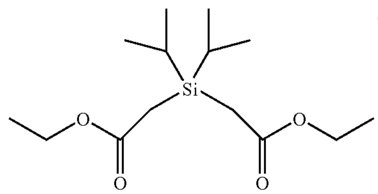 | δ 1.58 (heptet, 2H J = 7.2 Hz), 1.24 (d, 12H, J = 7.2 Hz). |
| Diethyl 2,2'-(dimethylsilanediyl)diacetate (IED2) | 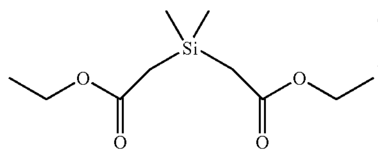 | δ 4.09 (q, 4H, J = 7.0 Hz), 1.99 (s, 4H), 1.24 (t, 6H, J = 7.0 Hz), 1.12 (heptet, 2H, J = 6.5 Hz), 1.06 (d, 12H, J = 6.5 Hz) |
| Diethyl 2,2'-(diisobutylsilanediyl)diacetate (IED3) | 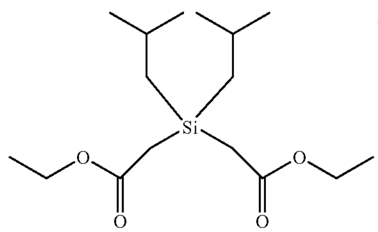 | δ 4.10 (q, 4H, J = 7.0 Hz), 2.03 (s, 4H), 1.87 (theptat, 2H, J = 6.5 Hz), 1.25 (t, 6H, J = 7.0 Hz), 0.96 (d, 12H, J = 6.5 Hz), 0.75 (d, 4H, J = 6.5 Hz) |

Procatalyst Compositions.

All manipulations are carried out under an inert atmosphere. A series of olefin polymerization procatalysts are prepared using a procatalyst precursor comprising magnesium, titanium, alkoxide and halide moieties. The composition is prepared by reacting magnesium diethoxide, titanium tetraethoxide, and titanium tetrachloride, in a mixture of orthocresol, ethanol and chlorobenzene at a temperature of about 75° C. for about 2 hours. The solid reaction product is precipitated by removing ethanol from the solution (by heating to about 90° C.), washing with isooctane and drying the recovered solids. The resulting composition comprises primarily a compound of the empirical formula: Mg$_3$Ti(OC$_2$H$_5$)$_8$Cl$_2$.

This precursor composition is next converted to procatalyst compositions by contact with a 50/50 volume mixture of TiCl$_4$ and chlorobenzene. In each preparation, approximately 3 grams of the precursor are added to a 150 mL flask. The mixture of TiCl$_4$ and chlorobenzene (60 mL) is added to the flask and subjected to stirring (250 rpm). Approximately 2.4 mmol of the respective internal electron donor is added and then the flask is heated to 115° C. where it is maintained for 1 hour. The resulting slurry is then filtered while hot through a fitted disc at the bottom of the flask.

The solids are then contacted twice with 60 mL of the 50/50 volume mixture of TiCl$_4$ in chlorobenzene at 115° C. for 30 minutes. The resulting solid product is collected by filtration, washed three times with 70 mL aliquots of room temperature isooctane, and dried in a stream of dry nitrogen for several hours.

Properties for the resultant procatalyst compositions are provided in Table 2.

TABLE 2

| Donor | % wt Ti | % wt Mg | % wt OEt | % wt DEP | % wt Donor |
|---|---|---|---|---|---|
| DIBP-1 | 2.89 | 17.37 | 0.3 | 0.3 | 16.0 |
| IED1 | 3.31 | 16.88 | 0.6 |  | 14.3 |
| IED2 | 3.23 | 17.61 | 1.1 |  | ≧3.6 |
| DIBP-2 | 2.91 | 18.65 | 0.1 | 0.8 | ≧5.9 |
| IED3 | 2.57 | 17.60 | 0.2 |  | ≧5.2 |

DEP = diethyl phthalate
DiBP = diisobutyl phthalate
IED = internal electron donor (from Table 1)
OEt = ethoxide
% = weight percent based on total weight of the procatalyst composition
Metal analysis by x-ray fluorescence analysis
Donor analysis by gas chromatography III. Polymerization.

Catalyst performance and resultant polymer properties for catalysts containing silyl glutarate are provided in Table 3.

Polymerization studies are also conducted using a 1-gallon (3.8 L) autoclave reactor. The external electron donor dicyclopentyldimethoxysilane (270 µmol) is combined with triethylaluminum (7.2 mL of a 5% wt. solution in isooctane) and allowed to age for 0.5 minutes before use. This mixture is then combined with the catalyst slurry (0.2 or 0.3 mL of a 5 percent slurry in mineral oil) and allowed to stand for an additional 20 minutes. Propylene (1375 g) is loaded into the reactor and the temperature of the reactor is equilibrated at 25° C. Hydrogen is added. The reactor is then heated to 62° C. and the premixed catalyst slurry is injected. The temperature is then raised to 67° C. where polymerization is allowed to continue for the remainder of the 60-minute reaction period.

TABLE 3

Polymerization performance data for the catalyst compositions made using silyl glutarates

| ID # | IED | Ti % | EED/Ti | EED | g PP | BD | PP | $H_2$ scc | MFR | XS % | PDI | $T_{MF}$, ° C. |
|---|---|---|---|---|---|---|---|---|---|---|---|---|
| *1 | DIBP-1 | 2.89 | 29 | D | 376 | 0.388 | 24.9 | 2500 | 8.3 | 3.1 | 4.95 | 171.43 |
| 2 | IED1 | 3.31 | 26 | D | 381 | 0.282 | 25.2 | 2000 | 4.3 | 2.5 | 4.56 | 171.81 |
| 3 | IED1 | 3.31 | 26 | D | 359 | 0.274 | 23.7 | 2500 | 5.7 | 2.0 | 4.58 | 171.64 |
| 4 | IED2 | 3.23 | 27 | D | 291 | 0.310 | 19.2 | 2000 | 2.3 | 3.6 | 5.12 | 171.26 |
| *5 | DIBP-2 | 2.91 | 27 | D | 345 | 0.382 | 34.5 | 3000 | 4.2 | 3.4 | 4.73 | 171.99 |
| *6 | DIBP-2 | 2.91 | 27 | D | 311 | 0.388 | 31.1 | 3000 | 5.7 | 3.6 | 4.72 | 171.57 |
| 7 | IED3 | 2.57 | 30 | D | 202 | 0.367 | 20.2 | 3000 | 6.0 | 3.9 | 4.53 | 171.52 |
| 8 | IED3 | 2.57 | 30 | D | 201 | 0.354 | 20.1 | 3000 | 6.7 | 4.2 | 4.46 | 171.20 |

* = comparative
BD = bulk density, g/cc
D = dicyclopentyldimethoxysilane
DiBP—diisobutylphthalate
EED = external electron donor
g PP = g polymer produced
IED = internal electron donor (Table 3)
PP = kg polymer produced/g catalyst-hr
Ti = percent weight titanium in catalyst It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A catalyst composition comprising:
a procatalyst comprising a combination of a magnesium moiety, a titanium moiety and an internal electron donor comprising a silyl glutarate; and
a cocatalyst.

2. A The catalyst composition of claim 1 comprising:
a silyl glutarate having the structure (I)

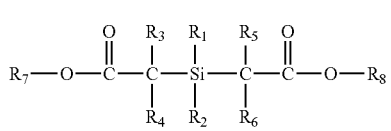

(I)

wherein $R_1$-$R_8$ are the same or different, each of $R_1$ and $R_2$ is selected from the group consisting of hydrogen and a saturated hydrocarbyl group having 1-6 carbon atoms, each of $R_3$-$R_6$ is selected from the group consisting of hydrogen and a hydrocarbyl group having 1-10 carbon atoms, each of $R_7$ and $R_8$ is selected from a hydrocarbyl group having 1-2 carbon atoms, and $R_1$, $R_2$, $R_7$ and $R_8$ are simultaneously not a methyl group.

3. The catalyst composition of claim 2 wherein each of $R_1$ and $R_2$ is selected from a saturated hydrocarbyl group having 1-4 carbon atoms.

4. The catalyst composition of claim 2 wherein the silyl glutarate is a member selected from the group consisting of diethyl 2,2'-(diisopropylsilanediyl)diacetate.

5. The catalyst composition of claim 1 wherein the silyl glutarate has the structure (I)

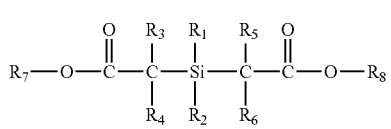

(I)

wherein $R_1$-$R_8$ are the same or different, each of $R_1$-$R_6$ is selected from the group consisting of hydrogen, a substituted hydrocarbyl group having 1 to 20 carbon atoms, an unsubstituted hydrocarbyl group having 1 to 20 carbon atoms, and combinations thereof, and each of $R_7$-$R_8$ is selected from the group consisting of a substituted hydrocarbyl group having 1 to 20 carbon atoms, an unsubstituted hydrocarbyl group having 1 to 20 carbon atoms, and combinations thereof.

6. The catalyst composition of claim 5 wherein $R_1$ and $R_2$ are the same or different and each is selected from the group consisting of hydrogen, a $C_1$-$C_6$ alkyl group, and combinations thereof.

7. The catalyst composition of claim 5 wherein $R_1$ and $R_2$ are the same or different and each is selected from the group consisting of a methyl group, an ethyl group, a propyl group, an isopropyl group, a butyl group, an isobutyl group and combinations thereof.

8. The catalyst composition of claim 5 wherein each of $R_1$ and $R_2$ is a methyl group.

9. The catalyst composition of claim 5 wherein each of $R_1$ and $R_2$ is an isopropyl group.

10. The catalyst composition of claim 5 wherein each of $R_1$ and $R_2$ is an isobutyl group.

11. The catalyst composition of claim 5 wherein $R_7$ and $R_8$ are the same or different and each is selected from the group consisting of a $C_1$-$C_6$ alkyl group.

12. The catalyst composition of claim 5 wherein each of $R_7$ and $R_8$ is an ethyl group.

13. The catalyst composition of claim 12 wherein each of $R_1$ and $R_2$ is a methyl group.

14. The catalyst composition of claim 12 wherein each of $R_1$ and $R_2$ is an isopropyl group.

15. The catalyst composition of claim 12 wherein each of $R_1$ and $R_2$ is an isobutyl group.

16. The catalyst composition of claim 5 wherein the internal electron donor comprises an electron donor component selected from the group consisting of a phthalate, ethyl benzoate, a diether, and combinations thereof.

17. The catalyst composition of claim 5 comprising a member selected from the group consisting of an external electron donor, a mixed external electron donor, an activity limiting agent, and combinations thereof.

18. The catalyst composition of claim 17 wherein the external electron donor comprises an alkoxysilane.

19. The catalyst composition of claim 17 comprising an activity limiting agent selected from the group consisting of a carboxylic acid ester, a diether, a diol ester, and combinations thereof.

20. A process for producing an olefin-based polymer comprising:
    contacting, under polymerization conditions, an olefin with the catalyst composition of claim 1; and
    forming an olefin-based polymer.

\* \* \* \* \*